US00PP27236P3

(12) United States Plant Patent
Schoone

(10) Patent No.: US PP27,236 P3
(45) Date of Patent: Oct. 4, 2016

(54) ***PHALAENOPSIS* ORCHID PLANT NAMED 'ENDLESS LOVE'**

(50) Latin Name: *Phalaenopsis hybrida*
Varietal Denomination: Endless Love

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 93 days.

(21) Appl. No.: 14/121,473

(22) Filed: Sep. 10, 2014

(65) Prior Publication Data

US 2015/0089701 P1 Mar. 26, 2015

Related U.S. Application Data

(60) Provisional application No. 61/882,106, filed on Sep. 25, 2013.

(30) Foreign Application Priority Data

Sep. 26, 2013 (NL) ..... PBR OPS1049

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Endless Love' particularly characterized by flowers which are white with a little yellow and some red/purple in the labellum; plants which may be propagated economically and uniformly using tissue culture; plants which produce more than one inflorescence; long and sturdy inflorescences; and relatively short, dark-green foliage.

2 Drawing Sheets

Latin name of the genus and species of the plant claimed: *Phalaenopsis hybrida.*

Variety denomination: 'Endless Love'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Endless Love'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Endless Love' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Endless Love' originated from a cross made by the inventor in 2001 in Strengweg, Heemskerk, The Netherlands. The female or seed parent is the *Phalaenopsis* cultivar designated 'Timothy Christopher', unpatented. The male or pollen parent is an unnamed cultivar of *Phalaenopsis amabilis*, unpatented. The new *Phalaenopsis* 'Endless Love' was discovered and selected by the inventor as a single flowering plant within the progeny of the stated cross in a controlled environment in 2009 in Strengweg, Heemskerk, The Netherlands.

Asexual reproduction of the new *Phalaenopsis* cultivar by tissue culture (mericloning) was first performed in July, 2009 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Endless Love', which in combination distinguish this *Phalaenopsis* as a new and distinct cultivar:

1. flowers which are white with a little yellow and some red/purple in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Endless Love', the female parent 'Timothy Christopher' is about 7 cm in size and has more yellow in the labellum, the male parent cultivar of *Phalaenopsis amabilis* is about 4 cm in size and has more yellow in the labellum, whereas the flowers of 'Endless Love' are about 3.5 cm in size and have less yellow in the labellum.

Presently, the commercial cultivar to which 'Endless Love' can be meaningfully compared is 'Silly Tommy' (unpatented). The flowers of 'Endless Love' are about 3.5 cm in size and have a little yellow In the labellum, whereas the flowers of 'Silly Tommy' are about 6 cm in size and have more and darker yellow in the labellum.

BRIEF DESCRIPTION OF THE PHOTOGRAPHS

The accompanying photographs illustrate the overall appearance of the new *Phalaenopsis* 'Endless Love' showing the colors as true as is reasonably possible with colored reproductions of this type. Colors in the photographs may differ slightly from the color values cited in the detailed botanical description, which accurately describe the color of 'Endless Love'.

DETAILED BOTANICAL DESCRIPTION

Figure 1:
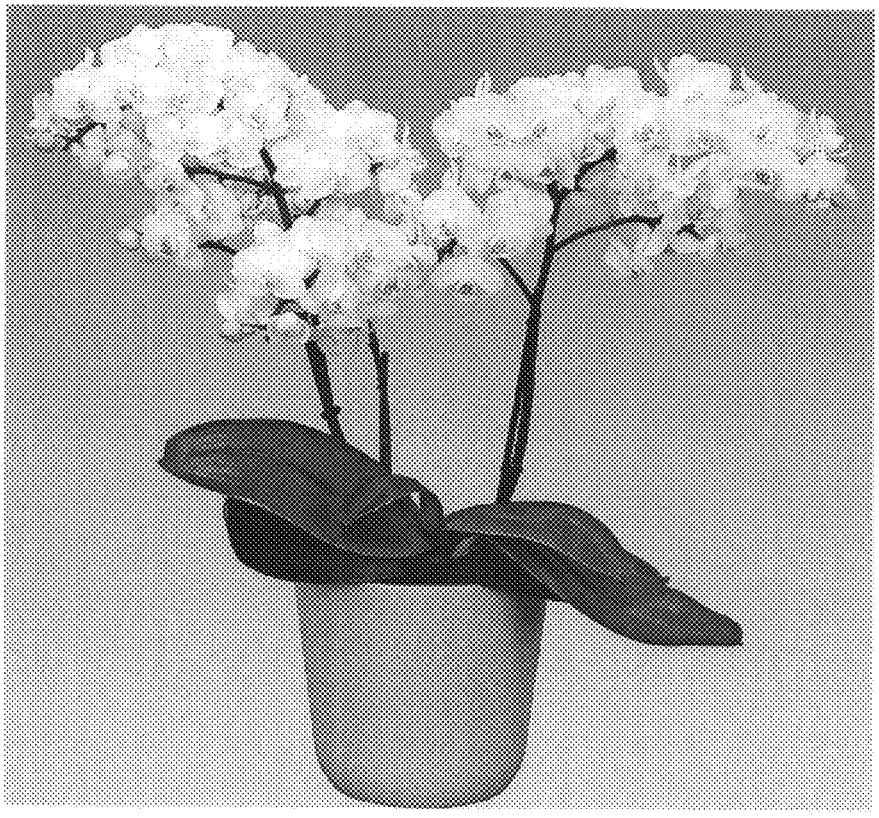
FIG. 1 shows a side view perspective of a typical flowering plant of 'Endless Love' in a 12 cm pot, at 16 months of age.

The new *Phalaenopsis* cultivar 'Endless Love' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Endless Love' as grown in a greenhouse in Strengweg, Heemskerk, The Netherlands, under conditions which closely approximate those generally used in commercial practice. Initially, the ideal temperature to grow plants of 'Endless Love' is 27° C. during the day and at night. Then, during the flowering phase of 'Endless Love', the ideal growing temperature is 20-22° C. during the day and 18° C. at night. Light levels for growing 'Endless Love' are a minimum of 5,000 lux and a maximum of 10,000 lux. A balanced fertilizer with level of 200 ppm N, 87 ppm P, 168 ppm K is applied. Duration of growth of 'Endless Love' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Endless Love' plants described is 12 months after potting.

Classification:

*Botanical.—Phalaenopsis hybrida.*

Parentage:

*Female or seed parent.—Phalaenopsis* cultivar designated 'Timothy Christopher', unpatented.

*Male or pollen parent.*—Unnamed cultivar of *Phalaenopsis amabilis*, unpatented.

Propagation:

*Type.*—Tissue culture (mericloning).

*Rooting habit and description.*—Fleshy; approximately 3 mm-5 mm wide and greyed/green in color (RHS 190B); freely branching. It takes 12 weeks for plants growing in tissue culture to initiate roots.

Plant:

*Size at maturity.*—Height (from bottom of pot to highest flower): about 38 cm. Spread: about 41 cm.

*Growth habit.*—Small, green leaves (RHS 137A/RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 to 4 racemes with flowers appear.

Foliage:

*Quantity per plant.*—About 8 leaves are produced before flowering.

*Arrangement and attachment.*—Alternate, clasping.

*Overall shape of leaf.*—Oval: the tip is blunt and asymmetric.

*Texture* (*upper* & *underside*).—Smooth and leathery.

*Pubescence.*—None.

*Mature leaf length.*—About 14 cm.

*Mature leaf width.*—About 7 cm.

*Mature leaf thickness.*—About 2 mm.

*Mature leaf color.*—Upper side: green (RHS 137A/N137A). Edges and at the base yellow/green (RHS 144A). Under side: green (RHS 146A).

*Leaf base.*—Acute.

*Margin.*—Entire.

*Venation.*—Pattern: parallel. Color of midvein: Upper side: green (RHS N137A). Under side: green (RHS 143A).

Inflorescence description:

*Appearance.*—Upright to slightly pendant, racemose inflorescence with bilaterally symmetrical flowers that open in succession beginning with the lowermost flower.

*Raceme.*—Quantity per plant: about 2 to 4. Number of flowers per raceme: about 20-30. Length: about 30 cm.

*Peduncle.*—Diameter: about 5 mm. Strength: strong. Aspect: upright. Texture: glabrous and smooth. Color: yellow/green (RHS 144A).

*Buds.*—Height (from base to tip): about 12 mm. Diameter (at midpoint): about 10 mm. Shape: oval with a bump on the side. Color: yellow/green (RHS 144C/RHS 144D). Orientation: same as flowers (forward facing).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 to 4 racemes appear with about 20 to 30 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
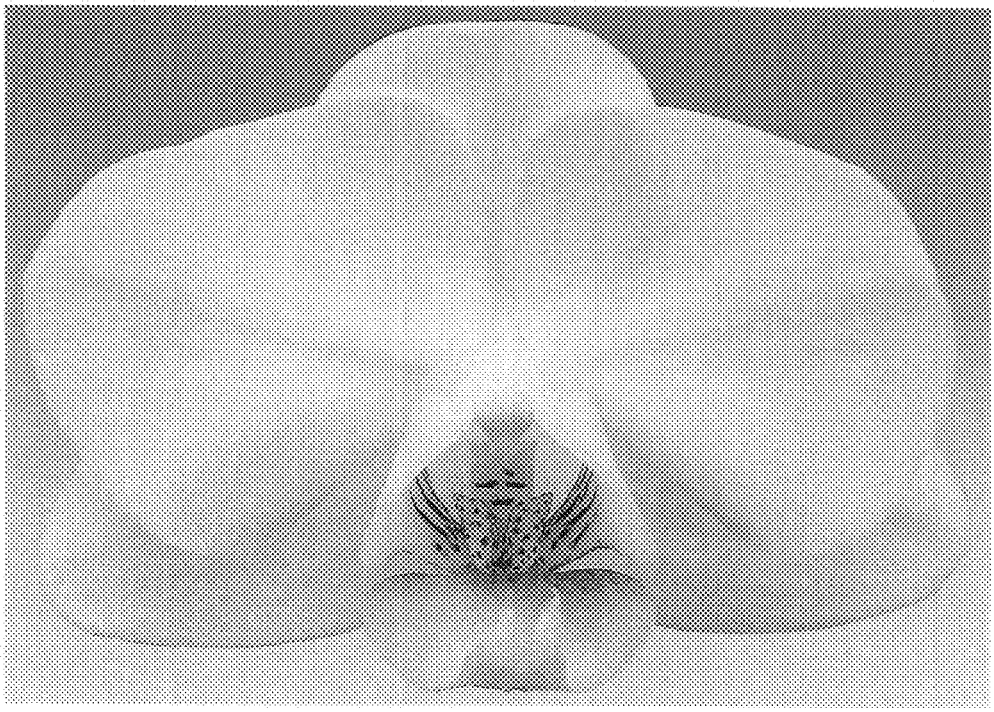
FIG. 2 shows a close-up view of the typical flower of 'Endless Love'.

*Flower*.—Rate of opening: Flowers fully opened about 2 to 3 days after petal and sepal separation. Orientation at opening: slanted upward and outward. Shape: Typical shape of *Phalaenopsis*; see FIG. 2. Size (of single bloom): Height: about 35 mm. Diameter: about 42 mm.

*Petals*.—Quantity and arrangement: three petals and three sepals that are trimerous and arranged in 2 overlapping whorls. Inner whorl of 3 petals is comprised of 2 lateral petals and a labellum. Petals are more pronounced than sepals. 2 lateral petals: Overall shape: broadly ovate, little triangular and weakly cupped. Apex: oval, little pointy. Margin: entire and weakly undulate. Base: broadly ovate. Length: about 22 mm. Width: about 21 mm. Texture: Upper surface: smooth and satiny. Under surface: smooth and satiny. Color (when fully opened): upper and under side: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin of the midlobe and the lateral lobes: entire and weakly undulate. Apex of the midlobe and the lateral lobes: oval. Length midlobe: about 15 mm. Width midlobe (not flattened): about 12 mm. Length lateral lobe: about 14 mm. Width lateral lobe (not flattened): about 15 mm. Depth of tube created by lateral lobes: about 17 mm. Texture of midlobe and lateral lobes: Upper and under surface: smooth and satiny. Color (when fully opened): Midlobe upper side: main color is white (RHS NN155C). In the corners some yellow (RHS 8C) and medium red/purple spots (RHS 70B). At the base few red/purple spots (RHS 70B). Under side: main color is white (RHS NN155C). The corners are yellow (RHS 8C) with a yellow edge (RHS 8A). At the base some red/purple (RHS 70A). Lateral lobes, upper side: main color is white (RHS NN155C). From base medium red/purple stripes (RHS 70A). Under edge is yellow (RHS 8C). Under side: white (RHS NN155C). Cirrhi: Small (about 3 mm). Color: white (RHS NN155C). Pestle (Callosities): Length: about 3 mm. Width (not flattened): about 4 mm. Pubescence: None. Color: main color is white (RHS NN155C). On top a yellow haze (RHS 8D) and red/purple spots (RHS 70A).

*Sepals*.—Arrangement: Outer whorl comprises 3 sepals. Overall shape: elliptical and weakly cupped. Margin: entire and weakly undulate. Length: about 21 mm. Width: about 17 mm. Apex: rounded; dorsal has a small notch. Texture: Upper and under surface: smooth and satiny. Color (when fully opened): Upper side: Dorsal and lateral: white (RHS NN155C). Under side: Dorsal and lateral: white (RHS NN155C). Some have a yellow/green haze (RHS 150C/RHS 150D).

*Pedicel*.—Length: about 25 mm. Diameter: about 3 mm. Texture: glabrous and smooth. Color: main color is white (RHS NN155C), with close to the flower a yellow/green haze (RHS 145C). Some also have a red/purple haze (RHS 71A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 6 mm. Diameter: about 3 mm. Color: white (RHS NN155C).

*Pollinia*.—Quantity: two. Diameter: about 2 mm. Color: yellow/orange (RHS 17A).

*Ovary*.—Length: about 2 mm. Diameter: about 2 mm. Color: white (RHS N155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Endless Love', as illustrated and described herein.

* * * * *